United States Patent [19]

Sabo

[11] Patent Number: 5,501,214
[45] Date of Patent: Mar. 26, 1996

[54] NON-REBREATHING VALVE AND VALVE ELEMENT THEREFOR

[75] Inventor: Kristine K. Sabo, New Kensington, Pa.

[73] Assignee: Respironics, Inc., Murrysville, Pa.

[21] Appl. No.: 312,468

[22] Filed: Sep. 26, 1994

[51] Int. Cl.⁶ .............................. A61M 16/00; A62B 9/02
[52] U.S. Cl. ............................... 128/205.24; 128/202.28; 128/202.29; 128/203.11
[58] Field of Search .......................... 128/201.11, 201.28, 128/203.11, 205.24, 206.15, 205.13, 207.12, 205.17, 202.28, 202.29; 623/9; 137/846, 850

[56] References Cited

U.S. PATENT DOCUMENTS

| | | | |
|---|---|---|---|
| 3,363,833 | 1/1968 | Laerdal | 128/205.13 |
| 3,556,122 | 1/1971 | Laerdal | 128/205.24 |
| 4,622,964 | 11/1986 | Flynn | 128/205.24 |
| 4,774,941 | 10/1988 | Cook | 128/205.13 |
| 5,005,568 | 4/1991 | Loescher et al. | 128/202.28 |
| 5,109,840 | 5/1992 | Daleiden | 128/205.13 |
| 5,279,289 | 1/1994 | Kirk | 128/205.23 |
| 5,357,951 | 10/1994 | Ratner | 128/205.24 |

*Primary Examiner*—Christopher A. Bennett
*Assistant Examiner*—V. Srivastava
*Attorney, Agent, or Firm*—Reed Smith Shaw & McClay

[57] ABSTRACT

A duck-bill valve element and a non-rebreathing valve (NRV) incorporating same. The duck-bill valve element is formed of flexible, resilient material and includes a peripheral portion continuously and sealingly attached to a housing of the NRV and a sealing portion contiguous with and extending radially inwardly of the peripheral portion, whereby the sealing portion is operable to releasably contact an internal valve seat of the valve housing. A hollow, wedge-shaped formation is contiguous with and projects from a first surface of the sealing portion. The wedge-shaped formation has a base defining an opening in the sealing portion and a distal end terminating in a slot. The valve element further includes integral structure for preventing inversion of the wedge-shaped formation under pressure applied to the wedge-shaped formation. The duck-bill valve element and the NRV may be employed in a breathing apparatus gas flow circuit between a source of respiratory gas and a patient interface component such as a respiratory mask.

5 Claims, 3 Drawing Sheets

NON-REBREATHING VALVE AND VALVE ELEMENT THEREFOR

FIELD OF THE INVENTION

The present invention relates in general to valve devices and, more particularly, to a valve adapted for use in breathing apparatus such as respiration assistance apparatus or anesthesia administration equipment.

BACKGROUND OF THE INVENTION

Non-rebreathing valves or NRVs are commonly used in an assortment of anesthesia administration equipment and respiration assistance apparatus including, inter alia, ventilators, resuscitators and sleep apnea treatment devices. The NRV is typically situated in the breathing apparatus gas flow circuit between a source of respiratory gas (e.g., ambient or pressurized air, pressurized oxygen and/or anesthetic gas) and a patient interface means such as a nasal or oral/nasal mask, an endotracheal (intubation) tube or nasal prongs. The function of the NRV is to act essentially as a two-way check valve. More particularly, when it is desired to deliver respiratory gas to the patient, the NRV permits such flow. When the patient exhales, however, the NRV vents the patient's expiratory gases while temporarily stopping the flow of respiratory gas responsive to back pressure created by the patient's expiratory efforts. In this manner, the NRV effectively prevents mixing of the patient's expiratory gases with the delivered respiratory gas whereby the patient does not "rebreathe" his expiratory gases.

Although their functions are essentially the same, NRVs assume a broad variety of structural configurations and levels of functional sophistication. Because of its relative simplicity in construction and low resistance to administered respiratory gas flow, a commercially popular NRV is the type commonly known as a "duck-bill" valve. A duck-bill valve derives its name from the peculiar shape of its valve element. That is to say, a duck-bill valve element typically comprises a thin, resilient diaphragm that is secured at its periphery to a valve housing and from which projects, in the direction of administered respiratory gas flow, a hollow, wedge-like extension that terminates in a small slot and generally resembles the shape of a duck bill.

The duck-bill valve element is constructed such that its slot is normally closed. However, in response to a flow of respiratory gas, which may arise from negative pressure associated with a patent's inspiration and/or delivery of respiratory gas under positive pressure, the slot opens to permit the respiratory gas to flow to the patient's airway. When the patient thereafter exhales, the back pressure exerted by the patient's expiratory gases closes the slot and displaces the valve element from its valve seat whereupon the expiratory gases are diverted to and discharged from suitable exhaust port means provided in the valve housing.

Moreover, duck-bill NRVs, like many other NRVs, may be employed simply to exhaust the patient's expiratory gases or, alternatively, they may be used in conjunction with mechanisms that are designed to create a phenomenon known as positive end expiratory pressure or PEEP. PEEP is desirable in certain instances, e.g., in assisting the breathing of a chronic pulmonary obstruction disorder (COPD) patient, where it is necessary to effect a somewhat elevated resistance to the patient's expiratory efforts to thereby promote the onset of inspiration at the end of the expiration phase of the patient's respiratory cycle. Typically, the mechanisms for effecting PEEP are adjustable to set the appropriate level of respiratory resistance.

Examples of presently known duck-bill valves are provided in U.S. Pat. Nos. 3,363,833, 3,556,122, 4,774,941, 5,109,840 and 5,279,289. Ironically, the primary feature which renders duck-bill valves particularly desirable for use in breathing apparatus, namely, a thin, flexible valve element that offers minimal resistance to respiratory gas flow, is a source of potentially serious malfunctions in such valves. Specifically, should the exhalation efforts of the patient be extremely forceful, such as, for example, when the patient coughs, the sudden imposition of high-level impulses of back pressure on the valve element may cause the duck-bill portion of the valve element diaphragm to invert. Under these circumstances, the duck-bill would point in the direction of the administered respiratory gas flow and the slot thereof would be caused to close under the influence of the applied respiratory gas. As a consequence, the supply of respiratory gas to the patient would become effectively occluded whereby the patient may experience harmful or even fatal respiratory distress, particularly if the patient is unconscious or is not being closely monitored by medical personnel.

Perhaps recognizing although not specifically identifying the need to prevent inversion of the duck-bill portions of their valve elements, the valves disclosed in U.S. Pat. Nos. 3,363,833, 3,556,122 and 5,109,840 disclose valve housings which incorporate various and sometimes elaborate structures upstream of the duck bill which permit respiratory gas to flow through the duck bill but, by virtue of their location, would appear to prevent the duck-bill from inverting. U.S. Pat. No. 5,279,289, on the other hand, expressly provides for a retainer ring upstream of the duck-bill valve element to "support" the valve element. In any event, even if the valve housing components disclosed in these patents effectively prevent inversion of the duck-bill, the very presence of such structures renders the valves unduly complicated in design and, therefore, commensurately expensive to manufacture.

An advantage exists, therefore, for a duck-bill non-rebreathing valve which is simple in design, economical to manufacture and which precludes inversion of the duck-bill valve element under extreme operating conditions.

SUMMARY OF THE INVENTION

In accordance with the present invention, there is provided an improved duck-bill non-rebreathing valve (NRV) adapted for use in breathing apparatus such as anesthesia administration equipment and respiratory assistance apparatus. The duck-bill NRV may be situated in the breathing circuit between a source of respiratory gas (e.g., ambient or pressurized air, pressurized oxygen and/or anesthesia gas) and a patient interface means such as a nasal or oral/nasal mask, an endotracheal tube or nasal prongs.

The duck-bill NRV of the present invention comprises a thin, resilient valve element in the form of a diaphragm adapted to be secured at its periphery to a valve housing and from which projects, in the direction of administered respiratory gas flow, a hollow, wedge-shaped formation that terminates in a small slot and generally resembles the shape of a duck bill. Unlike duck-bill NRVs heretofore known in the art, however, the instant duck-bill valve element does not require (nor does the NRV housing possess) any structure upstream of the duck-bill valve element for supporting the duck-bill formation against unintended inversion. More specifically, the present invention provides a novel duck-bill valve element that relies not upon the valve housing but instead utilizes integral valve element support means for inversion protection.

Accordingly to a presently preferred embedment, the valve element support means comprises means, preferably located at the upstream surface of the valve element, for stiffening a sealing portion of the valve element from which the duck-bill formation projects. As presently contemplated, the stiffening means desirably assume the form of annular support ring means provided on the valve element sealing portion. Desirably, the annular support ring means circumscribe the opening of and project in a direction generally opposite to the duck-bill formation. Most preferably, the valve element support means is formed or molded integrally with the valve element upon manufacture thereof.

With a duck-bill valve element so constructed, the duck-bill NRV of the present invention offers effective protection against inversion of its valve element while producing an assembly of uncomplicated yet rugged design, comparatively low cost to manufacture and reliable operation.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
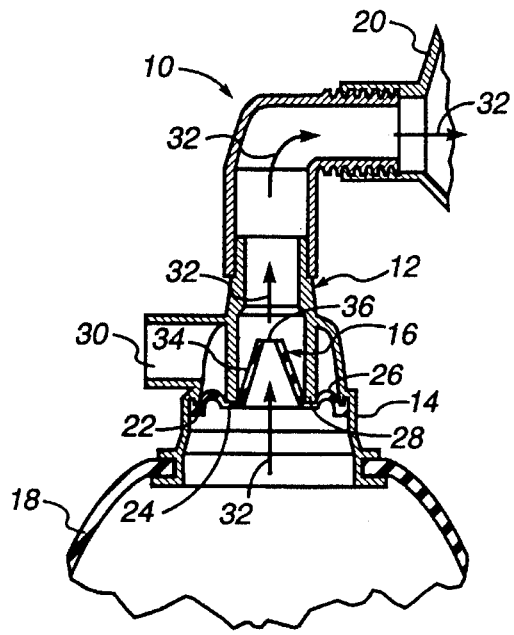
FIG. 1 is an elevational cross-section view of a conventional duck-bill NRV properly functioning within a breathing assistance apparatus.
Figure 2:
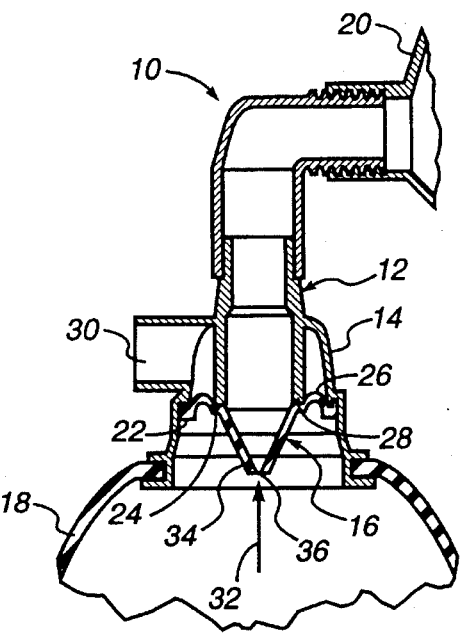
FIG. 2 is a view similar to FIG. 1 wherein the duck-bill portion of the NRV valve element is shown in an inverted, malfunctioning position.

Referring to FIGS. 1 and 2, there is depicted a conventional breathing apparatus 10 within which is installed a non-rebreathing valve (NRV) 12 including a housing 14 and a duck-bill valve element 16. For purpose of illustration, but not limitation, apparatus 10 is shown as a resuscitator apparatus commonly known as a "squeeze bag" or "bag-valve-mask" type resuscitator, the general operation of which is well known to those skilled in the subject art. Apparatus 10 includes a compressible, self-restoring bag 18 for delivering respiratory gas (e.g., ambient or pressurized air, pressurized oxygen or a combination of such gases) to a patient's airway through the duck-bill valve element 16 and a suitable patient interface means 20 such as a nasal or oral/nasal mask, intubation tube or nasal prongs. It will thus be appreciated that breathing apparatus 10 may also be, inter alia, a ventilator, a sleep apnea treatment apparatus or an anesthesia administration device.

The duck-bill valve element 16 is typically a unitary diaphragm member formed of thin, flexible, resilient material such as silicone rubber or the like. The outermost peripheral portion 22 of such valve element is normally continuously and sealingly affixed by suitable adhesives and/or clamping means to the valve housing 14. Extending radially inwardly of and contiguous with the peripheral portion 22 is a sealing portion 24 which may include a generally semi-toroidal region 26 for rendering the valve element less resistant to the pressure generated by the patient's expiratory efforts. As is known, except when the patient is exhaling, the sealing portion 24 typically contacts an internal valve housing seat 28 and operates to effect a gas tight seal between the interior of the apparatus 10 and discharge port means 30 provided in the housing 14 which communicate with the ambient atmosphere. This seal is further enhanced when the apparatus 10 is delivering respiratory gas through the valve element 16 to the airway of the patients as is represented by arrows 32.

Contiguous with and projecting from a first surface of the sealing portion 24 is a hollow, wedge-shaped formation 34 that generally resembles the shape of a duck-bill. The base of the wedge-shaped formation 34 defines an opening in the sealing portion 24 and the distal end of the wedge-shaped formation terminates in a small slot 36. Regardless of the specific breathing apparatus within which it is deployed, the NRV 12, as is the NRV of the present invention to be described hereinafter, is installed in the breathing circuit between a source of selected respiratory gas and the patient interface means 20 such that the duck-bill formation 34 points in the direction of the flow of the administered respiratory gas. FIG. 1 reflects the situation wherein the slot 36 is substantially expanded by the pressure of the respiratory gas flow. Should the patient exhale or the respiratory gas flow be stopped, the slot 36 closes. Once the slot is closed, the patient's expiratory gases flow in a direction opposite to arrows 32 to thereby exert a back pressure on the duck-bill formation 34 which causes the sealing portion 24 to separate from sealing engagement with the internal valve housing seat 28, whereby the expiratory gas are exhausted through discharge port means 30. So long as the patient's respiration proceeds according to substantially uneventful phases of inspiration and expiration, the NRV 12 functions quite satisfactorily for its intended purposes.

If, however, the patient's exhalation efforts become exceptionally forceful such as, for example, when the patient coughs, the sudden impingement of high-level impulses of back pressure on the duck-bill formation 34 may cause the formation to invert in the manner depicted in FIG. 2. Should this occur, the duck-bill formation would point in the direction of the administered respiratory gas flow and the slot 36 thereof would be urged to close under the influence of the applied respiratory gas (which is represented again by an arrow numbered 32). Such a scenario represents more than a simple inconvenience in that it temporarily disables the breathing apparatus 10. Indeed, under these conditions, the supply of respiratory gas to the patient becomes effectively occluded whereby the patient may experience harmful or possibly fatal respiratory distress, particularly if the patient is unconscious or is not being closely monitored by medical personnel.

Figure 3:
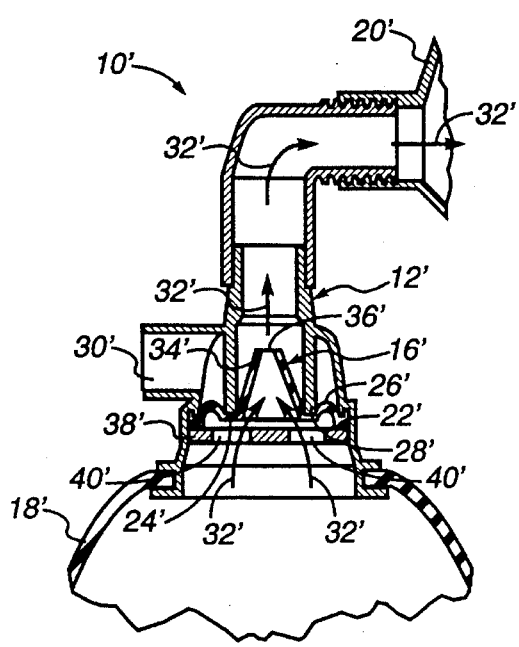
FIG. 3 is a view similar to FIG. 1 of another conventional duck-bill NRV properly functioning in a breathing apparatus wherein the valve housing includes support structure to preclude inversion of the duck-bill valve element.

To avoid potential inversion of the duck-bill formation 32, it has been suggested to provide means upstream of the duck-bill valve element to support the valve element when it is subjected to extreme back pressures that may be exerted by the patient. An example of such an arrangement is shown in FIG. 3. The breathing apparatus of that figure is identified by reference numeral 10' and is constructed and functions substantially similarly to the apparatus 10 discussed hereabove. Hence, the components of apparatus 10' which have the same reference numerals as components identified in FIGS. 1 and 2, but which are distinguished by prime symbols, may be considered to be the substantial equivalents in structure and function to their counterparts in FIGS. 1 and 2 and thus will not be described in detail. For brevity, therefore, only that structure in FIG. 3 which materially departs in structure and/or function from that disclosed in FIGS. 1 and 2 will be addressed herebelow.

In this regard, the primary distinction between apparatus 10 and apparatus 10' is the provision, either as an additional valve assembly component or as part of the valve housing 14', of support means 38' upstream of the duck-bill valve element 16' to prevent inversion of the duck-bill formation 34'. In the present context, the term "upstream" relates to the direction of administered respiratory gas flow and refers to that side of the valve element 16' where the respiratory gas (whose flow is represented by arrows 32') enters the valve element. Support means 38' may be a valve assembly component distinct from both the valve element and the valve housing, or it may be integral with the housing 14'. The support means typically assumes the form of a cage-like retainer ring or a grate which resists inversion of the duck-bill formation 34' but which includes one or more openings 40' to permit the passage of respiratory gas.

While effective for preventing inversion of its duck-bill valve element, an NRV constructed generally in accordance with NRV 12', i.e., having valve element inversion protection means either formed integrally with the valve housing 14' or provided as a separate and additional valve component, results in an NRV valve assembly that is needlessly complex in design and commensurately costly to manufacture.

Figure 4:
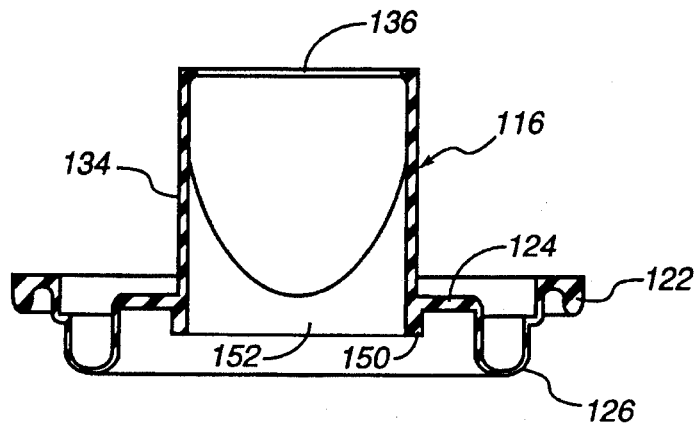
FIG. 4 is an elevational cross-section view of a duck-bill valve element constructed according to the instant invention.
Figure 5:
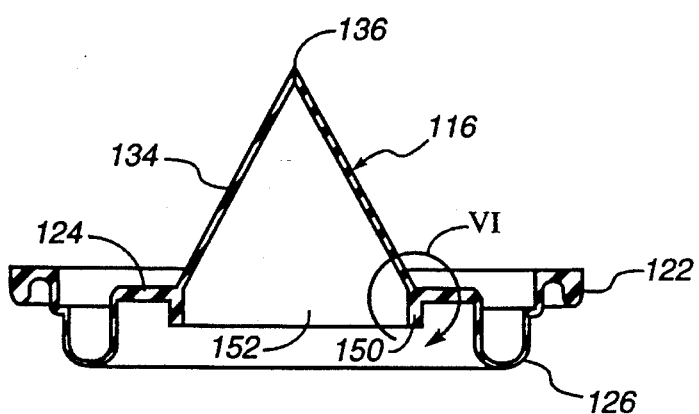
FIG. 5 is an elevational cross-section view of the duck-bill valve element of FIG. 4 taken from a perspective shifted 90° with respect to the cross-sectional view shown in FIG. 4.

FIGS. 4 and 5 reveal a presently preferred embodiment of a duck-bill valve element constructed in accordance with the instant invention and identified herein by reference numeral 116. Like the above-described duck-bill valve element 16, valve element 116 preferably comprises a unitary diaphragm member formed of thin, flexible, resilient material such as silicone rubber or the like. Valve element 116 includes an outermost peripheral portion 122 that is adapted to be continuously and sealingly affixed by suitable adhesives and/or clamping means to a valve housing, as will be discussed later herein in connection with the descriptions of FIGS. 7 and 8. Extending radially inwardly of and continuous with the peripheral portion 122 is a sealing portion 124 which may include, as shown, a substantially semi-toroidal or substantially U-shaped region 126 for rendering the valve element less resistant to the pressure generated by the patient's expiratory efforts.

Similar to valve element 16, the sealing portion 124 of valve element 116 is adapted to releasably contact internal valve housing seat to effect a gas tight seal between the interior of the apparatus within which the valve element 116 is disposed and discharge port means provided in the valve housing. This seal is augmented when respiratory gas is being delivered to the patient.

Figure 7:
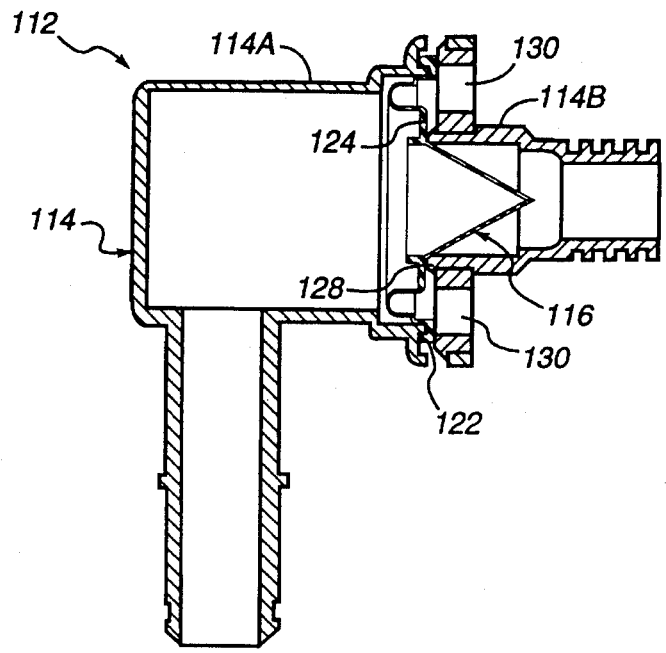
FIG. 7 is an elevational cross-section view of an NRV including a duck-bill valve element according to the present invention.
Figure 8:
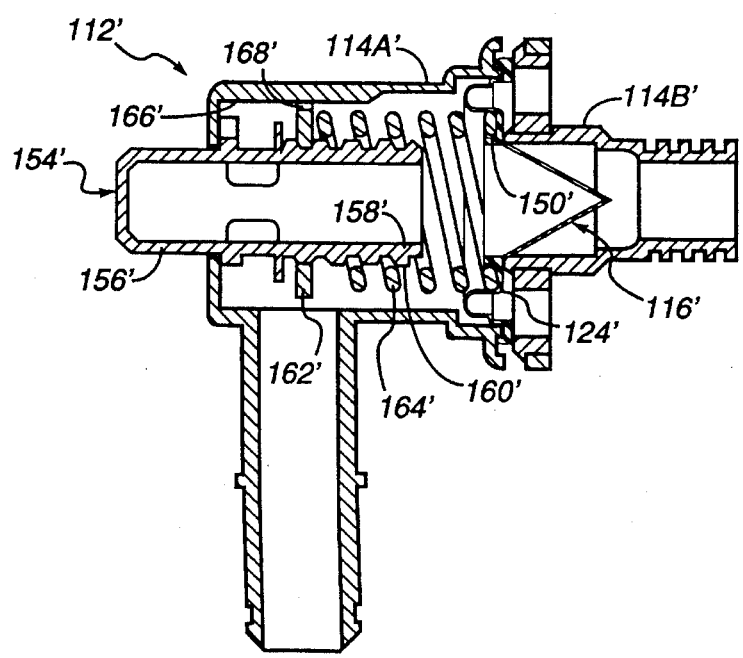
FIG. 8 is an elevational cross-section view of a portion of an NRV including a duck-bill valve element according to the present invention and a mechanism for adjusting the positive end expiratory pressure (PEEP) resistance exerted by the duck-bill valve against a patient's expiratory efforts.

Contiguous with and projecting from a first or "downstream" surface of the sealing portion 124 is a hollow, wedge-shaped formation 134 that terminates at its distal end in a small slot 136 and generally resembles the shape of a duck-bill. As seen in FIGS. 7 and 8, the duck-bill formation 134 points in the direction of applied respiratory gas flow. Normally, the slot 136 is closed as depicted in FIG. 5. When respiratory gas is flowing, however, the slot opens to permit passage of the gas therethrough similar to the manner in which the respiratory gas flows through the valve element 16 of FIGS. 1 and 3.

Figure 6:
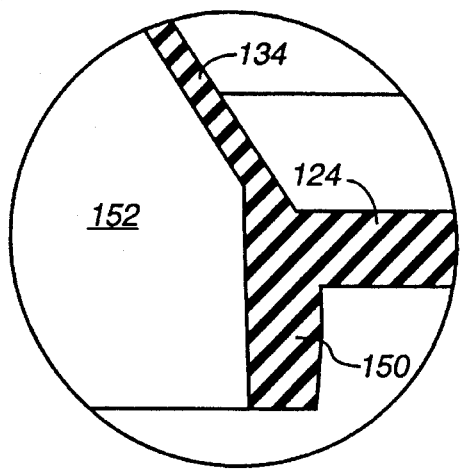
FIG. 6 is an enlarged view of that portion of the valve element encompassed by arrow VI of FIG. 5.

As seen in FIGS. 4 through 6, the valve element 116 further comprises valve element support means 150 which preferably project from a second or "upstream" surface of the sealing portion 124 in a direction generally opposite to the duck-bill formation 134. The valve element support means desirably comprises means for stiffening the sealing portion 124 from which the duck-bill formation 134 extends. The stiffening means preferably comprise annular ring means circumscribing an opening 152 defined in the sealing portion 124 by the base of the duck-bill formation 134. Although preferably constructed as a continuous annular ring, the annular ring means may also be fabricated as one or more protrusions which sufficiently stiffen the sealing portion 124 so as to prevent excessive flexure and possible inversion of the duck-bill formation 134 under the influence of excessive back pressure, e.g., pressure impulses generated by a patient's coughing. The valve element support means 150 may be fabricated separate from and then integrally attached by adhesive or other suitable fastening means to the upstream surface of the valve element 116. Most preferably, however, the valve element support means is formed or molded integrally with the valve element upon manufacture thereof.

FIG. 7 illustrates the valve element 116 of the present invention as installed in a nonadjustable, non-rebreathing valve (NRV) 112, which NRV may serve as a component in the breathing circuit of any of the aforementioned breathing apparatus.

The NRV 112 includes a housing 114 which may be formed of separate housing portions 114A and 114B between which the peripheral portion 122 of valve element 116 may be continuously and sealingly adhered or clamped (as illustrated.) The sealing portion 124 normally sealingly contacts an internal valve housing seat 128 to effect a gas tight seal between the interior of the breathing apparatus and discharge port means 130 provided in the valve housing 112. This seal is enhanced when respiratory gas is being delivered to the patient. When the patient exhales, the sealing portion 124 separates from valve seat 128 under the influence of the expiratory gas pressure and the expiratory gas is permitted to exit through discharge port means 130.

FIG. 8 depicts the instant valve element, identified in this figure by reference numeral 116', installed in non-rebreathing valve 112' which possesses a mechanism for adjusting the positive end expiratory pressure (PEEP) resistance exerted by the valve element against a patient's expiratory efforts. Valve element 116' is shown to be sealingly clamped between valve housing elements 114A' and 114B' in a manner similar to valve element 116 shown in FIG. 7. Moreover, the basic structure and function of valve element 116' is essentially identical to that previously described in connection with valve element 116.

The PEEP adjustment mechanism includes a control member 154' rotatably supported in valve housing portion 114A'. A first end 156' of the control number 154' projects through an end wall of the valve housing portion 114A' whereby it may be grasped and selectively rotated by an operator. A second end 158' of the control member is formed with threading 160'. An internally threaded member 162' threadedly engages the threading 160' such that, depending upon the direction of rotation of the control member 154', the member 162' may be translated in either of two directions along the control member, e.g., to the left or right in the NRV 112' as oriented in FIG. 8.

A compression-type coil spring 164' surrounds the second end 158' of the control member 154' One end of the spring 164' may either compressively abut or may be attached to internally threaded member 162'. The opposite end of the spring is adapted to receive the valve element support structure 150' and compressively abut the sealing portion 124' of valve element 116'. As the reader will appreciate, therefore, rotation of the control member 154' in a first direction will operate to increasingly compress spring 164' and correspondingly increase the force exerted by the spring against the sealing portion 124', thereby increasing the contacting force of the sealing portion against the valve seat 128' and the PEEP resistance experienced by the patient upon expiration. Rotation of the control member in the opposite direction will, of course, reduce PEEP resistance. To insure smooth travel of the internally threaded member 162', valve housing portion 114A' is preferably provided with at least one internally situated, elongated spline 166', or the like, which may be engaged by a slot 168' or other suitable formation provided in the outer periphery of member 162'.

It has been discovered through experimentation that an NRV constructed generally according to either NRV 112 of FIG. 7 or NRV 112' of FIG. 8, i.e., a nonadjustable or an adjustable NRV having installed therein the self-reinforced duck-bill valve element of the present invention, results in an assembly whereby inversion of the duck-bill formation of the valve element is effectively precluded, even under the imposition of extreme back pressures such as may arise when a patient coughs.

The present invention thus provides a novel inversion-resistant duck-bill valve element and novel NRVs incorporating such element which result in assemblies of uncomplicated yet rugged design, comparatively low cost to manufacture and reliable operation.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A valve element formed of flexible, resilient material, said valve element comprising:

a peripheral portion;

a sealing portion contiguous with and extending radially inwardly of said peripheral portion; and a hollow, wedge-shaped formation contiguous with and projecting from said sealing portion, said wedge-shaped formation having a base defining an opening in said sealing portion and a distal end terminating in a slot;

wherein said sealing portion includes means for preventing inversion of said wedge-shaped formation under pressure applied against said wedge-shaped formation, said means for preventing inversion of said wedge-shaped formation comprising a substantially semi-toroidal region projecting from said sealing portion in a direction generally opposite to said wedge-shaped formation.

2. The valve element of claim 1 further comprising an annular ring circumscribing said opening in said sealing portion for preventing excessive flexure and inversion of said wedge-shaped formation.

3. A non-rebreathing valve comprising:

a valve housing having an internal valve seat; and a valve element disposed in said valve housing and formed of flexible, resilient material, said valve element comprising:

a peripheral portion continuously and sealingly attached to said valve housing;

a sealing portion contiguous with and extending radially inwardly of said peripheral portion, said sealing portion being operable to releasable contact said valve seat;

a hollow, wedge-shaped formation contiguous with and projecting from said sealing portion, said wedge-shaped formation having a base defining an opening in said sealing portion and a distal end terminating in a slot;

wherein said sealing portion includes means integral with said valve element for preventing inversion of said wedge-shaped formation under pressure applied to said wedge-shaped formation, said means for preventing inversion of said wedge-shaped formation comprising a substantially semi-toroidal region projecting from said sealing portion in a direction generally opposite to said wedge-shaped formation.

4. The non-rebreathing valve of claim 3 further comprising an annular ring circumscribing said opening in said sealing portion for preventing excessive flexure and inversion of said wedge-shaped formation.

5. The non-rebreathing valve of claim 3 further comprising means for adjusting the force by which said sealing portion releasably contacts said valve seat.

* * * * *